United States Patent
Kita et al.

(10) Patent No.: US 9,562,034 B2
(45) Date of Patent: *Feb. 7, 2017

(54) ENDOPARASITE CONTROL AGENT

(71) Applicants: The University of Tokyo, Tokyo (JP); Nihon Nohyaku Co., Ltd., Tokyo (JP)

(72) Inventors: Kiyoshi Kita, Tokyo (JP); Akiyuki Suwa, Osaka (JP); Masatsugu Oda, Osaka (JP); Koji Tanaka, Osaka (JP)

(73) Assignees: The University of Tokyo, Tokyo (JP); Nihon Nohyaku Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/424,763

(22) PCT Filed: Aug. 29, 2013

(86) PCT No.: PCT/JP2013/073076
§ 371 (c)(1),
(2) Date: Feb. 27, 2015

(87) PCT Pub. No.: WO2014/034750
PCT Pub. Date: Mar. 6, 2014

(65) Prior Publication Data
US 2015/0266853 A1 Sep. 24, 2015

(30) Foreign Application Priority Data

Aug. 30, 2012 (JP) ................. 2012-189498

(51) Int. Cl.
| | |
|---|---|
| *C07D 307/68* | (2006.01) |
| *C07D 241/24* | (2006.01) |
| *C07D 401/12* | (2006.01) |
| *C07D 277/56* | (2006.01) |
| *C07D 327/06* | (2006.01) |
| *C07D 239/28* | (2006.01) |
| *C07D 231/14* | (2006.01) |
| *C07D 213/82* | (2006.01) |
| *C07D 333/38* | (2006.01) |
| *A61K 31/381* | (2006.01) |
| *A61K 31/39* | (2006.01) |
| *A61K 31/415* | (2006.01) |
| *A61K 31/426* | (2006.01) |
| *A61K 31/44* | (2006.01) |
| *A61K 31/4965* | (2006.01) |
| *A61K 31/505* | (2006.01) |
| *A61K 31/4439* | (2006.01) |
| *A61K 31/444* | (2006.01) |

(Continued)

(52) U.S. Cl.
CPC .......... *C07D 401/12* (2013.01); *A61K 31/381* (2013.01); *A61K 31/39* (2013.01); *A61K 31/415* (2013.01); *A61K 31/426* (2013.01); *A61K 31/44* (2013.01); *A61K 31/444* (2013.01); *A61K 31/4439* (2013.01); *A61K 31/497* (2013.01); *A61K 31/4965* (2013.01); *A61K 31/505* (2013.01); *C07D 213/82* (2013.01); *C07D 231/14* (2013.01); *C07D 239/28* (2013.01); *C07D 241/24* (2013.01); *C07D 277/56* (2013.01); *C07D 307/68* (2013.01); *C07D 327/06* (2013.01); *C07D 333/38* (2013.01); *C07D 401/00* (2013.01)

(58) Field of Classification Search
CPC .... C07C 233/69; C07C 235/46; C07C 317/32; C07C 323/42; C07D 213/56; C07D 231/12; C07D 401/04
USPC .......................................... 546/339; 514/346
See application file for complete search history.

(56) References Cited

U.S. PATENT DOCUMENTS

| | | | |
|---|---|---|---|
| 4,093,743 A | 6/1978 | Yabutani et al. | |
| 6,566,518 B1 * | 5/2003 | Maienfisch | A01N 43/40 544/335 |

(Continued)

FOREIGN PATENT DOCUMENTS

| | | | |
|---|---|---|---|
| EP | 0314422 A2 | | 5/1989 |
| EP | 0480258 | * | 9/1991 |

(Continued)

OTHER PUBLICATIONS

Chemical Abstracts STN Database Record for RN 320420-44-8, entered on Feb. 6, 2001.*

(Continued)

*Primary Examiner* — Noble Jarrell
*Assistant Examiner* — Daniel Carcanague
(74) *Attorney, Agent, or Firm* — Mintz Levin Cohn Ferris Glovsky and Popeo, P.C.; David G. Conlin; Christopher R. Cowles

(57) ABSTRACT

An object of the present invention is to provide a novel endoparasite control agent as a parasiticide, an antiprotozoal or the like. Provided is an endoparasite control agent comprising a carboxamide derivative represented by the general formula (I):

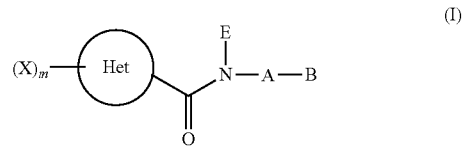

(wherein Het represents a 5- or 6-membered heterocyclic group), or
a salt thereof as an active ingredient.

8 Claims, No Drawings

(51) Int. Cl.
*A61K 31/497* (2006.01)
*C07D 401/00* (2006.01)

(56) References Cited

U.S. PATENT DOCUMENTS

| | | | | |
|---|---|---|---|---|
| 6,939,882 | B1* | 9/2005 | Cooke | A01N 43/40 514/311 |
| 7,332,509 | B2* | 2/2008 | Schaper | A01N 43/40 514/336 |
| 8,378,114 | B2* | 2/2013 | Oda | A01N 37/18 544/407 |
| 8,648,101 | B2* | 2/2014 | Suwa | A01N 43/40 514/357 |
| 9,447,042 | B2* | 9/2016 | Kita | A61K 31/166 |
| 2004/0087571 | A1 | 5/2004 | Brown et al. | |
| 2006/0052366 | A1* | 3/2006 | Mansfield | A01N 43/56 514/217.04 |
| 2007/0037753 | A1 | 2/2007 | Leban et al. | |
| 2009/0170924 | A1* | 7/2009 | Mansfield | A01N 43/08 514/448 |
| 2010/0048647 | A1 | 2/2010 | Suwa | |
| 2010/0249193 | A1* | 9/2010 | Andersch | A01N 43/40 514/341 |
| 2011/0136831 | A1 | 6/2011 | Oda et al. | |
| 2014/0005231 | A1* | 1/2014 | Bereznak | A01N 43/56 514/341 |
| 2014/0088157 | A1 | 3/2014 | Kita et al. | |
| 2014/0323736 | A1* | 10/2014 | Schwarz | A61K 31/166 546/316 |
| 2015/0259322 | A1* | 9/2015 | Kita | C07D 401/04 514/341 |

FOREIGN PATENT DOCUMENTS

| | | |
|---|---|---|
| EP | 1449841 A1 | 8/2004 |
| EP | 1997800 A1 | 12/2008 |
| JP | 53-9739 | 1/1978 |
| JP | 1-151546 A | 6/1989 |
| JP | 2012-87116 A | 5/2012 |
| WO | 01/14340 A1 | 3/2001 |
| WO | 02/057249 A1 | 7/2002 |
| WO | 02/057270 A1 | 7/2002 |
| WO | WO2006009054 * | 1/2006 |
| WO | 2007/060162 A1 | 5/2007 |
| WO | 2007/108483 A1 | 9/2007 |
| WO | 2008/003745 A1 | 1/2008 |
| WO | 2008/003746 A1 | 1/2008 |
| WO | 2008/062878 A1 | 5/2008 |
| WO | 2008/101975 A2 | 8/2008 |
| WO | 2008/101976 A1 | 8/2008 |
| WO | 2008/126922 A1 | 10/2008 |
| WO | 2009/012998 A1 | 1/2009 |
| WO | 2009/127718 A2 | 10/2009 |
| WO | 2010/106071 A1 | 9/2010 |
| WO | 2012/118139 A1 | 9/2012 |
| WO | 2013/064520 A1 | 5/2013 |
| WO | 2013/064521 A1 | 5/2013 |
| WO | WO 2013064461 * | 5/2013 |
| WO | WO2013076230 * | 5/2013 |
| WO | 2014/004064 A1 | 1/2014 |

OTHER PUBLICATIONS

Chemical Abstracts STN Database Record for RN 304692-85-1, entered on Nov. 28, 2000.*
Chemical Abstracts STN Database Record for RN 1197626-49-5, entered on Dec. 16, 2009.*
Chemical Abstracts STN Database Record for RN 1147333-09-2, entered on May 19, 2009.*
Kita, Kiyoshi, "New Strategies for the Development of Anti-Parasitic Drugs," Infection, Inflammation & Immunity, vol. 40(4):310-319 (2011).
Neal, R.A. et al., "In Vitro Anti-Leishmanial Activity of Compounds in Current Clinical Use for Unrelated Diseases", Drugs Under Experimental and Clinical Research, vol. 14, No. 10, 1988, pp. 621-628.
Vermeire, Jon J., et al., Cure of Hookworm Infection with a Cysteine Protease Inhibitor; Plos Neglected Tropical Diseases, vol. 6, No. 7, E1680, Jul. 2012, 8 pages.
Rhee, Sung-Whi, et al., Carbon-14 labeling of K777-HCl, a therapeutic agent for Chagas disease; J. of Labelled Compounds & Radiopharmaceuticals, vol. 56, No. 9-10, pp. 461-463, 2013, 3 pages.
Lepesheva, Galina I., et al., Sterol 14 alpha-Demethylase as a Potential Target for Antitrypanosomal Therapy: Enzyme Inhibition an Parasite Cell Growth; Chemistry and Biology, Current Biology, vol. 14, No. 11, pp. 1283-1293, 2007, 11 pages.
English translation of International Preliminary Report on Patentability issued in corresponding International Application No. PCT/JP2013/073076, Mar. 3, 2015, 6 pages.
Partial supplementary European search report issued in corresponding European Application No. 13833021, Feb. 15, 2016, 11 pages.

* cited by examiner

ENDOPARASITE CONTROL AGENT

RELATED APPLICATIONS

This application is the U.S. national stage pursuant to 35 U.S.C. §371, of U.S. international application Ser. No. PCT/JP2013/073076, filed Aug. 29, 2013, designating the United States and published in Japanese on Mar. 6, 2014, as publication WO 2014/034750 A1, which claims the benefit of Japanese application Ser. No. 2012-189498, filed Aug. 30, 2012. The entire contents of the aforementioned patent applications are incorporated herein by this reference.

TECHNICAL FIELD

The present invention relates an endoparasite control agent comprising a carboxamide derivative or a salt thereof as an active ingredient, and a method for controlling endoparasites, comprising orally or parenterally administering the endoparasite control agent.

BACKGROUND ART

Generally, parasitosis is caused by infestation of host animals with parasites such as unicellular protists (protozoa), multicellular helminths and arthropods. It is reported that the incidence of parasitosis in advanced countries has been remarkably decreased by improvement of environmental hygiene, but on a global scale, particularly in developing countries, parasitosis still widely prevails and causes tremendous damage.

In recent years, even in advanced countries, there has been an increasing trend in the incidence of parasitosis. This is partly because of introduction of infection sources via long- or short-term overseas travelers, and partly because of parasitic infection due to ingestion of food imports, frozen foods, raw meat, fish meat, etc. or via domestic animals and pets. Another problem is that immunodeficiency caused by mass administration of immunosuppressants, anticancer drugs, etc. or by AIDS etc. allows usually non-pathogenic or low-pathogenic parasites to express their pathogenicity and to cause opportunistic infection in hosts.

Further, parasitosis in domestic animals, such as pigs, horses, cattle, sheep, dogs, cats and domestic fowls, is a universal and serious economic problem. That is, parasitic infection of domestic animals causes anemia, malnutrition, debility, weight loss, and serious damage of intestinal tract walls, tissues and organs, and may result in decline in feed efficiency and productivity, leading to a great economic loss. Therefore, novel endoparasite control agents as a parasiticide, an antiprotozoal or the like have always been desired.

Certain kinds of carboxamide derivatives have been known to have microbicidal activity (see Patent Literature 1 to 13). Further, it is known that certain kinds of carboxamide derivative are effective against nematodes that may damage agricultural products (see Patent Literature 4 or 5). However, Patent Literature 1 to 13 has neither description nor suggestion that the disclosed compounds are effective against endoparasites in animals such as mammals and birds.

Furthermore, it has been reported that compounds that inhibit succinate-ubiquinone reductase (mitochondrial complex II), which is one of the respiratory enzymes of endoparasites, can serve as an endoparasite control agent (see Non Patent Literature 1), but it has been unknown whether carboxamide derivatives have inhibitory effect on succinate-ubiquinone reductase (mitochondrial complex II). Further, Patent Literature 1 to 13 has neither description nor suggestion on any inhibitory activity of the disclosed carboxamide derivatives on succinate-ubiquinone reductase (mitochondrial complex II).

CITATION LIST

Patent Literature

Patent Literature 1: JP-A 01-151546
Patent Literature 2: WO 2007/060162
Patent Literature 3: JP-A 53-9739
Patent Literature 4: WO 2007/108483
Patent Literature 5: WO 2008/126922
Patent Literature 6: WO 2008/062878
Patent Literature 7: WO 2008/101975
Patent Literature 8: WO 2008/101976
Patent Literature 9: WO 2008/003745
Patent Literature 10: WO 2008/003746
Patent Literature 11: WO 2009/012998
Patent Literature 12: WO 2009/127718
Patent Literature 13: WO 2010/106071

Non Patent Literature

Kiyoshi Kita, "Kansen (Infection)", Winter 2010, Vol. 40-4, 310-319

SUMMARY OF INVENTION

Technical Problem

In view of the above-described circumstances, an object of the present invention is to provide a novel endoparasite control agent as a parasiticide, an antiprotozoal or the like.

Solution to Problem

The present inventors conducted extensive research to solve the above-described problems. As a result, the present inventors found that a carboxamide derivative represented by the general formula (I), and a salt thereof have a high control effect against endoparasites. The present inventors further conducted a great deal of examination and then completed the present invention.

That is, the present invention relates to the following.
[1] An endoparasite control agent comprising a carboxamide derivative represented by the general formula (I):

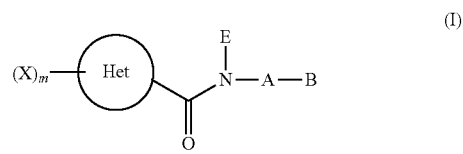

{wherein Het represents a 5- or 6-membered heterocyclic group, each X may be the same or different, and represents a halogen atom; a cyano group; a nitro group; an amino group; a ($C_1$-$C_6$) alkyl group; a halo ($C_1$-$C_6$) alkyl group; a ($C_1$-$C_6$) alkoxy group; a halo ($C_1$-$C_6$) alkoxy group; a ($C_1$-$C_6$) alkylthio group; a halo ($C_1$-$C_6$) alkylthio group; a ($C_1$-$C_6$) alkylsulfinyl group; a halo ($C_1$-$C_6$) alkylsulfinyl group; a ($C_1$-$C_6$) alkylsulfonyl group; or a halo ($C_1$-$C_6$) alkylsulfonyl group, m represents an integer of 0 to 5, A represents a $(C_1-C_8)$ alkylene group; or a substituted $(C_1-C_8)$ alkylene group having one or more substituents selected from a halogen atom, a $(C_1-C_6)$ alkyl group and a $(C_3-C_6)$ cycloalkyl group, with the proviso that the $(C_1-C_8)$ alkylene group and the substituted $(C_1-C_8)$ alkylene group may be modified by incorporation, into the carbon chain, of at least one group selected from —O—, —S—, —SO—, —SO$_2$— and —N(R)— (wherein R represents a hydrogen atom, a $(C_1-C_6)$ alkyl group, a $(C_3-C_6)$ cycloalkyl group, a $(C_1-C_6)$ alkylcarbonyl group or a $(C_1-C_6)$ alkoxycarbonyl group), and with the proviso that when the alkylene group or the substituted alkylene group having one or more substituents is a $(C_3-C_6)$ or $(C_3-C_8)$ alkylene group, or a $(C_2-C_6)$ or $(C_2-C_8)$ alkylene group modified by incorporation, into the carbon chain, of at least one group selected from —O—, —S—, —SO—, —SO$_2$— and —N(R)— (wherein R is as defined above), A may form a cyclic structure, E represents a hydrogen atom; a $(C_1-C_6)$ alkyl group; a $(C_3-C_6)$ cycloalkyl group; a $(C_1-C_6)$ alkoxy $(C_1-C_6)$ alkyl group; a $(C_1-C_6)$ alkylcarbonyl group; or a $(C_1-C_6)$ alkoxycarbonyl group, and B represents any of the moieties represented by the following B1 to B8:

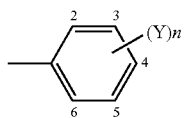
B1

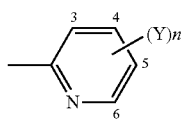
B2

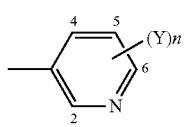
B3

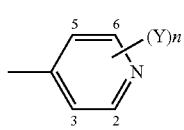
B4

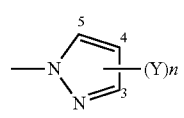
B5

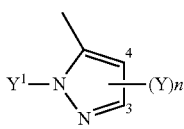
B6

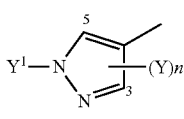
B7

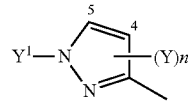
B8

(wherein each Y may be the same or different, and represents a halogen atom; a cyano group; a nitro group; a hydroxy group; a $(C_1-C_6)$ alkyl group; a halo $(C_1-C_6)$ alkyl group; a $(C_2-C_6)$ alkenyl group; a halo $(C_2-C_6)$ alkenyl group; a $(C_2-C_6)$ alkynyl group; a halo $(C_2-C_6)$ alkynyl group; a $(C_1-C_6)$ alkoxy group; a halo $(C_1-C_6)$ alkoxy group; a $(C_1-C_6)$ alkoxy $(C_1-C_6)$ alkoxy group; a $(C_2-C_6)$ alkenyloxy group; a halo $(C_2-C_6)$ alkenyloxy group; a $(C_2-C_6)$ alkynyloxy group; a halo $(C_2-C_6)$ alkynyloxy group; a $(C_1-C_6)$ alkylthio group; a halo $(C_1-C_6)$ alkylthio group; a $(C_1-C_6)$ alkylsulfinyl group; a halo $(C_1-C_6)$ alkylsulfinyl group; a $(C_1-C_6)$ alkylsulfonyl group; a halo $(C_1-C_6)$ alkylsulfonyl group; a $(C_1-C_6)$ alkoxycarbonyl group; a $(C_1-C_6)$ alkoxyimino $(C_1-C_3)$ alkyl group; a $(C_3-C_{30})$ trialkylsilyl group; a mono $(C_1-C_6)$ alkylsulfonylamino group; a mono halo $(C_1-C_6)$ alkylsulfonylamino group; a phenyl group; a substituted phenyl group having one or more substituents selected from group Z substituents on the ring; a phenoxy group; a substituted phenoxy group having one or more substituents selected from group Z substituents on the ring; a heterocyclic group; a substituted heterocyclic group having one or more substituents selected from group Z substituents on the ring; a heterocycloxy group; or a substituted heterocycloxy group having one or more substituents selected from group Z substituents on the ring, the group Z substituents are a halogen atom; a cyano group; a nitro group; a $(C_1-C_6)$ alkyl group; a halo $(C_1-C_6)$ alkyl group; a $(C_2-C_6)$ alkenyl group; a halo $(C_2-C_6)$ alkenyl group; a $(C_2-C_6)$ alkynyl group; a halo $(C_2-C_6)$ alkynyl group; a $(C_1-C_6)$ alkoxy group; a halo $(C_1-C_6)$ alkoxy group; a $(C_2-C_6)$ alkenyloxy group; a halo $(C_2-C_6)$ alkenyloxy group; a $(C_2-C_6)$ alkynyloxy group; a halo $(C_2-C_6)$ alkynyloxy group; a $(C_1-C_6)$ alkylthio group; a halo $(C_1-C_6)$ alkylthio group; a $(C_1-C_6)$ alkylsulfinyl group; a halo $(C_1-C_6)$ alkylsulfinyl group; a $(C_1-C_6)$ alkylsulfonyl group; a halo $(C_1-C_6)$ alkylsulfonyl group; a $(C_1-C_6)$ alkoxycarbonyl group; and a $(C_1-C_6)$ alkoxyimino $(C_1-C_3)$ alkyl group.

$Y^1$ represents a $(C_1-C_6)$ alkyl group, n represents an integer of 0 to 5, with the proviso that when n is an integer of 2 to 5, two adjacent Y groups may join together to form a $(C_3-C_5)$ alkylene group; a $(C_3-C_5)$ alkenylene group; a $(C_2-C_4)$ alkyleneoxy group; a $(C_1-C_3)$ alkylene dioxy group; or a halo $(C_1-C_3)$ alkylene dioxy group, and the numbers on each ring represent positions where the ring can be substituted by Y and the free bond extending from each ring is a bond between A and B)}, or a salt thereof as an active ingredient.

[2] The endoparasite control agent according to the above [1], wherein Het is any moiety selected from the following Het1 to Het17:

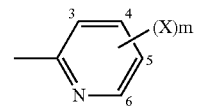
Het 1

-continued

Het 2
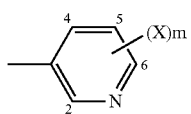

Het 3
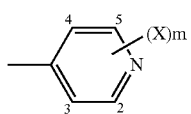

Het 4
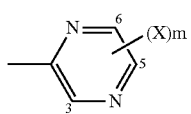

Het 5
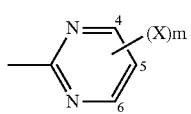

Het 6
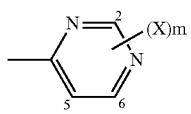

Het 7
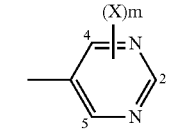

Het 8
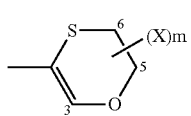

Het 9
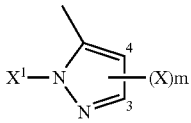

Het 10
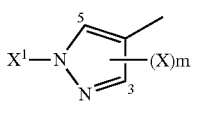

Het 11
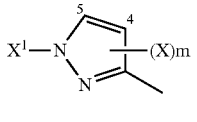

Het 12
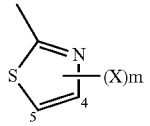

Het 13
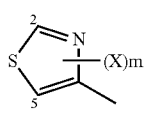

-continued

Het 14
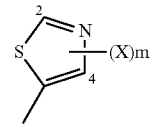

Het 15
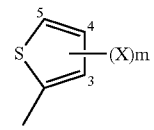

Het 16
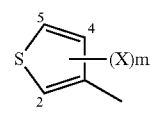

Het 17
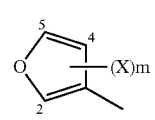

(wherein each X may be the same or different, and represents a halogen atom; a cyano group; a nitro group; an amino group; a ($C_1$-$C_6$) alkyl group; a halo ($C_1$-$C_6$) alkyl group; a ($C_1$-$C_6$) alkoxy group; a halo ($C_1$-$C_6$) alkoxy group; a ($C_1$-$C_6$) alkylthio group; a halo ($C_1$-$C_6$) alkylthio group; a ($C_1$-$C_6$) alkylsulfinyl group; a halo ($C_1$-$C_6$) alkylsulfinyl group; a ($C_1$-$C_6$) alkylsulfonyl group; or a halo ($C_1$-$C_6$) alkylsulfonyl group.

$X^1$ represents a ($C_1$-$C_6$) alkyl group; or a halo ($C_1$-$C_6$) alkyl group, m represents an integer of 0 to 5, and the numbers on each ring represent positions where the ring can be substituted by X and the free bond extending from each ring is a bond between Het and the carbonyl group in the general formula (I)).

[3] The endoparasite control agent according to the above [2], wherein Het is Het1, Het2, Het4, Het14 or Het15.

[4] The endoparasite control agent according to any one of the above [1] to [3], wherein A is a ($C_1$-$C_8$) alkylene group; or a substituted ($C_1$-$C_8$) alkylene group having one or more substituents selected from a halogen atom, a ($C_1$-$C_6$) alkyl group and a ($C_3$-$C_6$) cycloalkyl group.

[5] The endoparasite control agent according to any one of the above [1] to [4], wherein B is B1, B2 or B5.

[6] The endoparasite control agent according to the above [2], wherein Het is Het1, Het2, Het4, Het14 or Het15, each X may be the same or different, and is a halogen atom; a ($C_1$-$C_6$) alkyl group; or a halo ($C_1$-$C_6$) alkyl group, m is 1 or 2, A is a ($C_1$-$C_8$) alkylene group; or a ($C_1$-$C_8$) alkylene group substituted by a ($C_1$-$C_6$) alkyl group, E is a hydrogen atom, B is B1, B2 or B5, each Y may be the same or different, and is a halogen atom; a ($C_1$-$C_6$) alkyl group; a halo ($C_1$-$C_6$) alkyl group; a phenyl group; a substituted phenyl group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a phenoxy group; a substituted phenoxy group having one or more substituents selected from a halogen atom, a ($C_1$-$C_6$) alkyl group, a halo ($C_1$-$C_6$) alkyl group, a ($C_1$-$C_6$) alkoxy group and a halo $(C_1\text{-}C_6)$ alkoxy group on the ring; a pyridyl group; a substituted pyridyl group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring; a pyridyloxy group; or a substituted pyridyloxy group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring, and n is an integer of 1 to 3.

[7] The endoparasite control agent according to the above [2], wherein Het is Het1, Het2, Het4, Het14 or Het15, each X may be the same or different, and is a halogen atom; a $(C_1\text{-}C_6)$ alkyl group; or a halo $(C_1\text{-}C_6)$ alkyl group, m is 1 or 2, A is a $(C_1\text{-}C_8)$ alkylene group; or a $(C_1\text{-}C_8)$ alkylene group substituted by a $(C_1\text{-}C_6)$ alkyl group, E is a hydrogen atom, B is B1, each Y may be the same or different, and is a halogen atom; a $(C_1\text{-}C_6)$ alkyl group; a halo $(C_1\text{-}C_6)$ alkyl group; a phenyl group; a substituted phenyl group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring; a phenoxy group; a substituted phenoxy group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring; a pyridyl group; a substituted pyridyl group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring; a pyridyloxy group; or a substituted pyridyloxy group having one or more substituents selected from a halogen atom, a $(C_1\text{-}C_6)$ alkyl group, a halo $(C_1\text{-}C_6)$ alkyl group, a $(C_1\text{-}C_6)$ alkoxy group and a halo $(C_1\text{-}C_6)$ alkoxy group on the ring, and n is an integer of 1 to 3.

[8] A method for controlling endoparasites, comprising orally or parenterally administering an effective amount of the endoparasite control agent according to any one of the above [1] to [7] to a non-human mammal or a bird.

[9] A method for controlling endoparasites, comprising orally or parenterally administering an effective amount of the endoparasite control agent according to any one of the above [1] to [7] to a non-human mammal.

[10] The method according to the above [9], wherein the non-human mammal is a domestic animal.

Advantageous Effects of Invention

The present invention provides a compound useful as an endoparasite control agent which excels in performance as compared with the conventional art.

DESCRIPTION OF EMBODIMENTS

The definitions in the carboxamide derivative represented by the general formula (I) are described below.

The "$(C_1\text{-}C_8)$ alkylene group" refers to a straight alkylene group of 1 to 8 carbon atoms, for example, a methylene group, an ethylene group, a trimethylene group, a tetramethylene group, a pentamethylene group, a hexamethylene group, a heptamethylene group, an octamethylene group or the like. The "$(C_3\text{-}C_5)$ alkylene group" refers to a straight alkylene group of 3 to 5 carbon atoms, for example, a trimethylene group, a tetramethylene group, a pentamethylene group or the like. In the "substituted $(C_1\text{-}C_8)$ alkylene group having a substituent (s) selected from a halogen atom, a $(C_1\text{-}C_6)$ alkyl group and a $(C_3\text{-}C_6)$ cycloalkyl group," each substituent may be the same or different, and may be bound to any carbon atom in the alkylene group. The statement "the $(C_1\text{-}C_8)$ alkylene group and the substituted $(C_1\text{-}C_8)$ alkylene group may be modified by incorporation, into the carbon chain, of at least one group selected from —O—, —S—, —SO—, —SO$_2$— and —N(R)— (wherein R represents a hydrogen atom, a $(C_1\text{-}C_6)$ alkyl group, a $(C_3\text{-}C_6)$ cycloalkyl group, a $(C_1\text{-}C_6)$ alkylcarbonyl group or a $(C_1\text{-}C_6)$ alkoxycarbonyl group)" means that it is possible to form a moiety which is the same as the above-mentioned non-substituted or substituted straight $(C_1\text{-}C_8)$ alkylene group except for having an above-listed group attached to a terminal carbon atom or inserted between carbon atoms in the alkylene group. The specific examples include an ethyleneoxy group, an ethylenethio group, an ethylene sulfinyl group, an ethylene sulfonyl group, an ethylene amino group, a propyleneoxy group, a propylenethio group, a propylene sulfinyl group, a propylene sulfonyl group, a propylene amino group, —CH$_2$—CH$_2$—O—CH$_2$—, —CH$_2$—CH$_2$—S—CH$_2$— and —CH$_2$—CH$_2$—NH—CH$_2$—.

The "halogen atom" refers to a fluorine atom, a chlorine atom, a bromine atom or an iodine atom.

The "$(C_1\text{-}C_6)$ alkyl group" refers to a straight or branched alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, a neopentyl group, a n-hexyl group or the like. The "halo $(C_1\text{-}C_6)$ alkyl group" refers to a straight or branched alkyl group of 1 to 6 carbon atoms substituted by one or more halogen atoms which may be the same or different from each other, for example, a trifluoromethyl group, a difluoromethyl group, a perfluoroethyl group, a hexafluoroisopropyl group, a perfluoroisopropyl group, a chloromethyl group, a bromomethyl group, a 1-bromoethyl group, a 2,3-dibromopropyl group or the like. The "$(C_3\text{-}C_6)$ cycloalkyl group" refers to a cycloalkyl group of 3 to 6 carbon atoms, for example, a cyclopropyl group, a cyclobutyl group, a cyclopentyl group, a cyclohexyl group or the like.

The "$(C_2\text{-}C_6)$ alkenyl group" refers to a straight or branched alkenyl group of 2 to 6 carbon atoms, for example, a vinyl group, a propenyl group, a butenyl group or the like. The "halo $(C_2\text{-}C_6)$ alkenyl group" refers to a straight or branched alkenyl group of 2 to 6 carbon atoms substituted by one or more halogen atoms which may be the same or different from each other, for example, a fluorovinyl group, a difluorovinyl group, a perfluorovinyl group, a 3,3-dichloro-2-propenyl group, a 4,4-difluoro-3-butenyl group or the like.

The "$(C_2\text{-}C_6)$ alkynyl group" refers to a straight or branched alkynyl group of 2 to 6 carbon atoms, for example, an ethynyl group, a propynyl group, a butynyl group or the like. The "halo $(C_2\text{-}C_6)$ alkynyl group" refers to a straight or branched alkynyl group of 2 to 6 carbon atoms substituted by one or more halogen atoms which may be the same or different from each other, for example, a fluoroethynyl group, a perfluoropropynyl group, a 4,4,4-trifluoro-2-butynyl group or the like.

The "$(C_1\text{-}C_6)$ alkoxy group" refers to a straight or branched alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a neopentyloxy group, a n-hexyloxy group or the like.

The "halo ($C_1$-$C_6$) alkoxy group" refers to a straight or branched alkoxy group of 1 to 6 carbon atoms substituted by one or more halogen atoms which may be the same or different from each other, for example, a trifluoromethoxy group, a difluoromethoxy group, a perfluoroethoxy group, a perfluoroisopropoxy group, a chloromethoxy group, a bromomethoxy group, a 1-bromoethoxy group, a 2,3-dibromopropoxy group or the like.

The "($C_1$-$C_6$) alkoxy ($C_1$-$C_6$) alkoxy group" refers to a straight or branched alkoxy group of 1 to 6 carbon atoms having a straight or branched alkoxy group of 1 to 6 carbon atoms as a substituent at a substitutable position, for example, a methoxymethoxy group, an ethoxymethoxy group, a 1-methoxyethoxy group, a 2-methoxyethoxy group, a 1-ethoxyethoxy group, a 2-ethoxyethoxy group or the like.

The "($C_1$-$C_6$) alkoxy ($C_1$-$C_6$) alkyl group" refers to a straight or branched alkyl group of 1 to 6 carbon atoms having a straight or branched alkoxy group of 1 to 6 carbon atoms as a substituent at a substitutable position, for example, a methoxymethyl group, an ethoxymethyl group, a 1-methoxyethyl group, a 2-methoxyethyl group, a 1-ethoxyethyl group, a 2-ethoxyethyl group or the like.

The "($C_2$-$C_6$) alkenyloxy group" refers to a straight or branched alkenyloxy group of 2 to 6 carbon atoms, for example, a propenyloxy group, a butenyloxy group, a pentenyloxy group or the like. The "halo ($C_2$-$C_6$) alkenyloxy group" refers to a straight or branched alkenyloxy group of 2 to 6 carbon atoms substituted by one or more halogen atoms which may be the same or different from each other, for example, a fluorovinyloxy group, a difluorovinyloxy group, a perfluorovinyloxy group, a 3,3-dichloro-2-propenyloxy group, a 4,4-difluoro-3-butenyloxy group or the like.

The "($C_2$-$C_6$) alkynyloxy group" refers to a straight or branched alkynyloxy group of 2 to 6 carbon atoms, for example, a propynyloxy group, a butynyloxy group, a pentynyloxy group or the like. The "halo ($C_2$-$C_6$) alkynyloxy group" refers to a straight or branched alkynyloxy group of 2 to 6 carbon atoms substituted by one or more halogen atoms which may be the same or different from each other, for example, a fluoroethynyloxy group, a perfluoropropynyloxy group, a 4,4,4-trifluoro-2-butynyloxy group or the like.

The "($C_1$-$C_6$) alkylthio group" refers to a straight or branched alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a n-hexylthio group or the like. The "halo ($C_1$-$C_6$) alkylthio group" refers to a straight or branched alkylthio group of 1 to 6 carbon atoms substituted by one or more halogen atoms which may be the same or different from each other, for example, a trifluoromethylthio group, a difluoromethylthio group, a perfluoroethylthio group, a perfluoroisopropylthio group, a chloromethylthio group, a bromomethylthio group, a 1-bromoethylthio group, a 2,3-dibromopropylthio group or the like.

The "($C_1$-$C_6$) alkylsulfinyl group" refers to a straight or branched alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a n-hexylsulfinyl group or the like. The "halo ($C_1$-$C_6$) alkylsulfinyl group" refers to a straight or branched alkylsulfinyl group of 1 to 6 carbon atoms substituted by one or more halogen atoms which may be the same or different from each other, for example, a trifluoromethylsulfinyl group, a difluoromethylsulfinyl group, a perfluoroethylsulfinyl group, a perfluoroisopropylsulfinyl group, a chloromethylsulfinyl group, a bromomethylsulfinyl group, a 1-bromoethylsulfinyl group, a 2,3-dibromopropylsulfinyl group or the like.

The "($C_1$-$C_6$) alkylsulfonyl group" refers to a straight or branched alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a n-hexylsulfonyl group or the like. The "halo ($C_1$-$C_6$) alkylsulfonyl group" refers to a straight or branched alkylsulfonyl group of 1 to 6 carbon atoms substituted by one or more halogen atoms which may be the same or different from each other, for example, a trifluoromethylsulfonyl group, a difluoromethylsulfonyl group, a perfluoroethylsulfonyl group, a perfluoroisopropylsulfonyl group, a chloromethylsulfonyl group, a bromomethylsulfonyl group, a 1-bromoethylsulfonyl group, a 2,3-dibromopropylsulfonyl group or the like.

The "($C_1$-$C_6$) alkylcarbonyl group" refers to a straight or branched alkyl group of 1 to 6 carbon atoms bound to a carbonyl group, for example, a methylcarbonyl group, an ethylcarbonyl group, a n-propylcarbonyl group, an isopropylcarbonyl group, a n-butylcarbonyl group, a tert-butylcarbonyl group or the like.

The "($C_1$-$C_6$) alkoxycarbonyl group" refers to a straight or branched alkoxy group of 1 to 6 carbon atoms bound to a carbonyl group, for example, a methoxycarbonyl group, an ethoxycarbonyl group, a n-propoxycarbonyl group, an isopropoxycarbonyl group, a n-butoxycarbonyl group, a tert-butoxycarbonyl group or the like.

The "($C_1$-$C_6$) alkoxyimino ($C_1$-$C_3$) alkyl group" refers to a straight or branched alkoxy group of 1 to 6 carbon atoms bound to an imino ($C_1$-$C_3$) alkyl group, for example, a methoxyimino methyl group, an ethoxyimino methyl group, a n-propoxyimino methyl group, an isopropoxyimino ethyl group or the like.

The "($C_3$-$C_{30}$) trialkylsilyl group" refers to a straight or branched alkylsilyl group of 3 to 30 carbon atoms in total, for example, a trimethylsilyl group, a triethylsilyl group or the like.

The "mono($C_1$-$C_6$) alkylsulfonylamino group" refers to a straight or branched monoalkylsulfonylamino group of 1 to 6 carbon atoms, for example, a methylsulfonylamino group, an ethylsulfonylamino group, an isopropylsulfonylamino group or the like. The "mono halo ($C_1$-$C_6$) alkylsulfonylamino group" refers to a straight or branched monoalkylsulfonylamino group of 1 to 6 carbon atoms substituted by one or more halogen atoms which may be the same or different from each other, for example, a trifluoromethylsulfonylamino group or the like.

Examples of the cyclic structure that A can form include cyclopropane, cyclobutane, cyclopentane and cyclohexane.

The "($C_3$-$C_5$) alkenylene group" refers to a straight or branched alkenylene group of 3 to 5 carbon atoms having one or two double bonds therein, for example, a propenylene group, a 1-butenylene group, a 2-butenylene group, a pentenylene group or the like.

Examples of the "($C_2$-$C_4$) alkyleneoxy group" include —$CH_2$—$CH_2$—O—, —$CH_2$—$C(CH_3)_2$—O—, $CH_2$—$CH_2$—$CH_2$—O— and —$CH_2$—$CH_2$—$CH_2$—$CH_2$—O—.

The "($C_1$-$C_3$) alkylene dioxy group" refers to an alkylene dioxy group of 1 to 3 carbon atoms, for example, —O—$CH_2$—O—, —O—$CH_2$—$CH_2$—O—, —O—$CH_2$—$CH_2$—$CH_2$—O— or the like. The "halo ($C_1$-$C_3$) alkylene dioxy group" refers to an alkylene dioxy group of 1 to 3 carbon atoms substituted by one or more halogen atoms which may be the same or different from each other, for example, —O—$CF_2$—O—, —O—$CF_2$—$CF_2$—O—, —O—$CCl_2$—O— or the like.

The "heterocyclic group" refers to a 5- or 6-membered monocyclic aromatic or 3- or 6-membered monocyclic non-aromatic heterocyclic group containing, as ring atoms, a carbon atom(s) and 1 to 4 heteroatoms selected from an oxygen atom, a sulfur atom and a nitrogen atom; and also refers to a condensed heterocyclic group formed by condensation of such a monocyclic aromatic or non-aromatic heterocycle with a benzene ring or by condensation of such monocyclic aromatic or non-aromatic heterocycles (the heterocycles may be different from each other).

Examples of the "aromatic heterocyclic group" include monocyclic aromatic heterocyclic groups, such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl and triazinyl; and aromatic condensed heterocyclic groups, such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl and pyrazolotriazinyl.

Examples of the "non-aromatic heterocyclic group" include monocyclic non-aromatic heterocyclic groups, such as oxiranyl, thiiranyl, aziridinyl, oxetanyl, thietanyl, azetidinyl, pyrrolidinyl, piperidinyl, morpholinyl, thiomorpholinyl, piperazinyl, hexamethyleneiminyl, oxazolidinyl, thiazolidinyl, imidazolidinyl, oxazolinyl, thiazolinyl, imidazolinyl, dioxolyl, dioxolanyl, dihydrooxadiazolyl, 2-oxo-1,3-oxazolidin-5-yl, pyranyl, tetrahydropyranyl, thiopyranyl, tetrahydrothiopyranyl, 1-oxide tetrahydrothiopyranyl, 1,1-dioxide tetrahydrothiopyranyl, tetrahydrofuryl, dioxanyl, pyrazolidinyl, pyrazolinyl, tetrahydropyrimidinyl, dihydrotriazolyl and tetrahydrotriazolyl; and non-aromatic condensed heterocyclic groups, such as dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl and dihydrophthalazinyl.

Examples of a salt of the carboxamide derivative represented by the general formula (I) include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

In the carboxamide derivative represented by the general formula (I), Het is preferably any moiety selected from Het1 to Het16, and particularly preferably Het1, Het2, Het4, Het14 or Het15. X is preferably a halogen atom; a cyano group; a nitro group; an amino group; a $(C_1-C_6)$ alkyl group; a halo $(C_1-C_6)$ alkyl group; a $(C_1-C_6)$ alkoxy group; a halo $(C_1-C_6)$ alkoxy group; a $(C_1-C_6)$ alkylthio group; a halo $(C_1-C_6)$ alkylthio group; a $(C_1-C_6)$ alkylsulfinyl group; a halo $(C_1-C_6)$ alkylsulfinyl group; a $(C_1-C_6)$ alkylsulfonyl group; or a halo $(C_1-C_6)$ alkylsulfonyl group, and particularly preferably a halogen atom; a $(C_1-C_6)$ alkyl group; or a halo $(C_1-C_6)$ alkyl group. $X^1$ is preferably a $(C_1-C_6)$ alkyl group. m is particularly preferably 1 or 2.

A is preferably a $(C_1-C_8)$ alkylene group; or a substituted $(C_1-C_8)$ alkylene group having a substituent (s) which may be the same or different from each other and is/are selected from a halogen atom, a $(C_1-C_6)$ alkyl group and a $(C_3-C_6)$ cycloalkyl group. It is also preferred that the $(C_1-C_8)$ alkylene group and the substituted $(C_1-C_8)$ alkylene group are modified by incorporation, into the carbon chain, of at least one group selected from —O—, —S—, —SO—, —$SO_2$— and —N(R)— (wherein R represents a hydrogen atom, a $(C_1-C_6)$ alkyl group, a $(C_3-C_6)$ cycloalkyl group, a $(C_1-C_6)$ alkylcarbonyl group or a $(C_1-C_6)$ alkoxycarbonyl group). A is further preferably a $(C_1-C_8)$ alkylene group; or a substituted $(C_1-C_8)$ alkylene group having a $(C_1-C_6)$ alkyl group as a substituent, and particularly preferably an ethylene group; or an ethylene group substituted by a $(C_1-C_6)$ alkyl group. In the case where A can form a cyclic structure, preferable examples of the cyclic structure include cyclopropane, cyclobutane, cyclopentane and cyclohexane, and cyclopropane is particularly preferred. The "case where A can form a cyclic structure" encompasses a case where the alkylene group or the substituted alkylene group having one or more substituents is a $(C_3-C_6)$ or $(C_3-C_8)$ alkylene group, or a $(C_2-C_6)$ or $(C_2-C_8)$ alkylene group modified by incorporation, into the carbon chain, of at least one group selected from —O—, —S—, —SO—, —$SO_2$— and —N(R)— (wherein R is as defined above).

E is preferably a hydrogen atom; a $(C_1-C_6)$ alkyl group; a $(C_3-C_6)$ cycloalkyl group; a $(C_1-C_6)$ alkoxy $(C_1-C_6)$ alkyl group; a $(C_1-C_6)$ alkylcarbonyl group; or a $(C_1-C_6)$ alkoxycarbonyl group, and particularly preferably a hydrogen atom.

B is preferably any moiety selected from B1 to B8, particularly preferably B1, B2 or B5, and further preferably B1.

Y is preferably a halogen atom; a $(C_1-C_6)$ alkyl group; a halo $(C_1-C_6)$ alkyl group; a phenyl group; a substituted phenyl group having, on the ring, a substituent (s) which may be the same or different from each other and is/are selected from a halogen atom, a $(C_1-C_6)$ alkyl group, a halo $(C_1-C_6)$ alkyl group, a $(C_1-C_6)$ alkoxy group and a halo $(C_1-C_6)$ alkoxy group; a phenoxy group; a substituted phenoxy group having, on the ring, a substituent(s) which may be the same or different from each other and is/are selected from a halogen atom, a $(C_1-C_6)$ alkyl group, a halo $(C_1-C_6)$ alkyl group, a $(C_1-C_6)$ alkoxy group and a halo $(C_1-C_6)$ alkoxy group; a pyridyl group; a substituted pyridyl group having, on the ring, a substituent (s) which may be the same or different from each other and is/are selected from a halogen atom, a $(C_1-C_6)$ alkyl group, a halo $(C_1-C_6)$ alkyl group, a $(C_1-C_6)$ alkoxy group and a halo $(C_1-C_6)$ alkoxy group; a pyridyloxy group; or a substituted pyridyloxy group having, on the ring, a substituent (s) which may be the same or different from each other and is/are selected from a halogen atom, a $(C_1-C_6)$ alkyl group, a halo $(C_1-C_6)$ alkyl group, a $(C_1-C_6)$ alkoxy group and a halo $(C_1-C_6)$ alkoxy group. Y is particularly preferably a halogen atom; a halo $(C_1-C_6)$ alkyl group; or a substituted phenyl group having, on the ring, a substituent(s) which may be the same or different from each other and is/are selected from a halogen atom, a $(C_1-C_6)$ alkyl group, a halo $(C_1-C_6)$ alkyl group, a $(C_1-C_6)$ alkoxy group and a halo $(C_1-C_6)$ alkoxy group. $Y^1$ is preferably a $(C_1-C_6)$ alkyl group. n is preferably an integer of 1 to 3.

The carboxamide derivative represented by the general formula (I) can have one or more chiral centers or double bonds in the structural formula, and can exist as two or more kinds of optical isomers, diastereomers and geometric isomers. All mixtures of these isomers at any ratio are also included in the present invention.

The compound represented by the general formula (I) can be produced by Production Methods illustrated below. Alternatively, the production of the compound can be achieved by the production method described in JP-A 01-151546, WO 2007/060162, JP-A 53-9739, WO 2007/108483, WO 2008/101975, WO 2008/062878, WO 2008/101976, WO 2008/003745, WO 2008/003746, WO 2009/012998, WO 2009/127718 or WO 2010/106071, the method described in Shin-Jikken Kagaku Kouza 14 (Maruzen, Dec. 20, 1977), a modified method of the foregoing, or the like.

Production Method 1

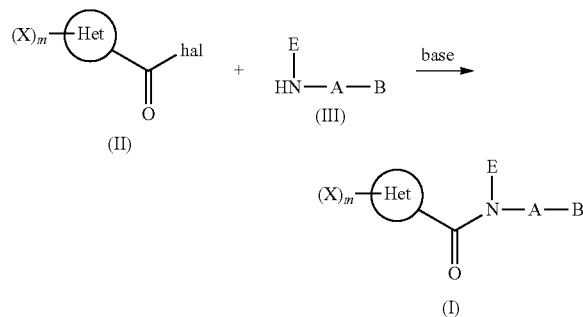

(In the formula, Het, X, A, E, B and m are as defined above, and hal represents a halogen atom.)

The carboxamide derivative represented by the general formula (I) can be produced by allowing an acid halide represented by the general formula (II) to react with an amine represented by the general formula (III) in the presence of a base in an inert solvent.

The reaction temperature in this reaction is usually from −20 to 120° C., and the reaction time is usually from 0.2 to 24 hours. The amine represented by the general formula (III) is usually used in a 0.8- to 5-fold molar amount relative to the acid halide represented by the general formula (II).

Examples of the base that can be used in the reaction include inorganic bases such as sodium hydroxide, potassium hydroxide, sodium carbonate, potassium carbonate, sodium hydrogencarbonate and potassium hydrogencarbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethyl aminopyridine. The base is usually used in a 0.5- to 10-fold molar amount relative to the acid halide represented by the general formula (II).

The reaction may be performed with or without a solvent. As the solvent, any solvent can be used unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate and butyl acetate; and polar solvents such as N,N-dimethylformamide, N,N-dimethylacetamide, dimethyl sulfoxide, 1,3-dimethyl-2-imidazolidinone, water and acetic acid. These inert solvents may be used alone or as a mixture of two or more kinds.

After the reaction is completed, the compound of interest is isolated from the post-reaction mixture according to a usual method. As needed, the compound of interest can be purified by recrystallization, column chromatography, etc.

The acid halide represented by the general formula (II) used for the reaction can be produced by the method described in known literature (for example, WO 05/115994, WO 01/42223, WO 03/066609, WO 03/066610, WO 03/099803, WO 03/099804, WO 03/080628 or the like) or a modified method thereof. The amine represented by the general formula (III) can be produced by the method described in WO 2007/108483 etc., or a modified method thereof.

Production Method 2

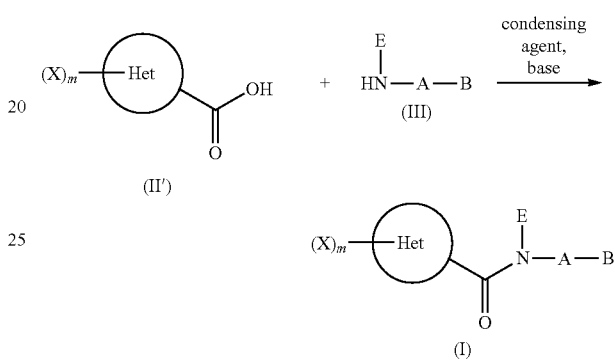

(In the formula, Het, X, A, E, B and m are as defined above.)

The carboxamide derivative represented by the general formula (I) can be produced by allowing a carboxylic acid represented by the general formula (II') to react with an amine represented by the general formula (III) in the presence of a condensing agent and a base in an inert solvent.

Examples of the condensing agent used in this reaction include diethyl phosphorocyanidate (DEPC), carbonyldiimidazole (CDI), 1,3-dicyclohexylcarbodiimide (DCC), 1-ethyl-3-(3-dimethylaminopropyl)carbodiimide hydrochloride, chlorocarbonic esters and 2-chloro-1-methylpyridinium iodide. The condensing agent is usually used in a 0.5- to 3-fold molar amount relative to the carboxylic acid represented by the general formula (II').

The reaction temperature, the reaction time, the base, the solvent, the isolation method and the like are in accordance with those of Production Method 1.

Representative examples of the carboxamide derivative of the general formula (I) which have been produced by Production Method 1, 2 or the like are shown in Table 1, but the present invention is not limited thereto. In Table 1, "Ph" represents a phenyl group, "Py" represents a pyridyl group, and "Ac" represents an acetyl group. "Het1" to "Het16" and "B1" to "B8" are as defined above, and "A1" to "A7" represent the moieties shown below. The physical property refers to a melting point (° C.) or a refractive index nD.

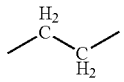

A1

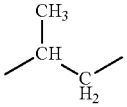

A2

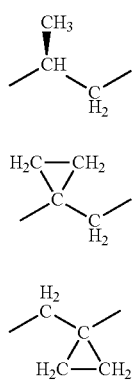

A3

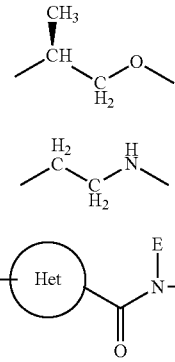

A6

A4

A7

A5

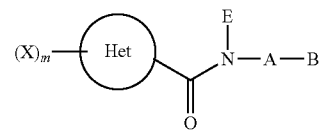

(I)

TABLE 1

| No. | $(X)_m, X^1$ | Het | E | A | B | $(Y)_n, Y^1$ | Physical property |
|---|---|---|---|---|---|---|---|
| 1 | 2-Cl | Het2 | H | A1 | B2 | 3-Cl-5-CF$_3$ | 105-106 |
| 2 | 2-NH$_2$-4-CF$_3$ | Het14 | H | A1 | B1 | 2,4-Cl$_2$ | 173.5-174.8 |
| 3 | 3-CF$_3$ | Het4 | H | A1 | B2 | 3-Cl-5-CF$_3$ | 130-131 |
| 4 | 3-CF$_3$ | Het4 | H | A1 | B1 | 2-Cl-4-(4-OCF$_3$—Ph) | 124-125 |
| 5 | 3-CH$_3$ | Het4 | H | A1 | B1 | 4-(4-OCF$_3$—Ph) | 122-123 |
| 6 | 2-CF$_3$ | Het2 | H | A1 | B1 | 2,4-Cl$_2$ | 133-139 |
| 7 | 3-CF$_3$ | Het15 | H | A1 | B1 | 2,4-Cl$_2$ | 67-70 |
| 8 | 2-CF$_3$ | Het2 | H | A1 | B1 | 2,4-Cl$_2$ | 133-139 |
| 9 | 3-CF$_3$ | Het4 | H | A1 | B1 | 2,4-Cl$_2$ | 110.2-111.2 |
| 10 | 3-CH$_3$ | Het4 | H | A2 | B1 | 2,4-Cl$_2$ | 164-166 |
| 11 | 3-CF$_3$ | Het4 | H | A1 | B1 | 2-Cl-4-F | 93.1-95.7 |
| 12 | 3-CF$_3$ | Het4 | H | A1 | B1 | 2-F-4-(4-OCF$_3$—Ph) | 126-127 |
| 13 | 3-Cl | Het4 | H | A5 | B1 | 2,4-Cl$_2$ | paste |
| 14 | 3-Cl | Het4 | H | A2 | B1 | 2,4-Cl$_2$ | 168 |
| 15 | 3-CF$_3$ | Het4 | H | A2 | B1 | 2,4-Cl$_2$ | 166-167 |
| 16 | 3-CF$_3$ | Het4 | H | A5 | B1 | 2,4-Cl$_2$ | 91-95 |
| 17 | 3-Cl | Het4 | H | A1 | B1 | 2-F-4-(4-OCF$_3$—Ph) | 136-137 |
| 18 | 3-CF$_3$ | Het4 | H | A4 | B1 | 2,4-Cl$_2$ | 125-128 |
| 19 | 3-CF$_3$ | Het4 | H | A1 | B1 | 2-Cl-4-CF$_3$ | 118-119 |
| 20 | 3-CF$_3$ | Het4 | H | A1 | B1 | 2-F-4-Cl | 132-133 |
| 21 | 3-CF$_3$ | Het4 | H | A1 | B1 | 2-Cl-4-O(3-Cl-5-CF$_3$—Py-2-yl) | 128.8-129.9 |
| 22 | 2-Cl | Het2 | H | A1 | B1 | 2-Cl-4-O(3-Cl-5-CF$_3$—Py-2-yl) | 137.8-139.3 |
| 23 | 3-Cl | Het4 | H | A2 | B1 | 2-F-4-Cl | 143.2-145.8 |
| 24 | 3-CF$_3$ | Het4 | H | A1 | B1 | 2,5-F$_2$-4-Cl | 110.3-112.9 |
| 25 | 2-Cl | Het2 | H | A1 | B1 | 2,5-F$_2$-4-Cl | 116-117.6 |
| 26 | 3-CF$_3$ | Het4 | H | A2 | B1 | 2-Cl-4,5-F$_2$ | 161.4-162.5 |
| 27 | 3-CF$_3$ | Het4 | H | A1 | B1 | 2-Cl-4,5-F$_2$ | 132.2-132.7 |
| 28 | 3-CF$_3$ | Het4 | H | A1 | B1 | 2,4-Cl$_2$-5-F | 123.3-125.5 |
| 29 | 2-Cl | Het2 | H | A1 | B1 | 2,4-Cl$_2$-5-F | 104.5-105 |
| 30 | 3-CH$_3$ | Het1 | H | A1 | B1 | 2,4-Cl$_2$ | 85 |
| 31 | 4-CF$_3$ | Het2 | H | A1 | B1 | 2,4-Cl$_2$ | 116-117 |
| 32 | 4-CF$_3$ | Het7 | H | A1 | B1 | 2,4-Cl$_2$ | 145.7-146.5 |
| 33 | 3-CF$_3$ | Het8 | H | A1 | B1 | 2,4-Cl$_2$ | 139 |
| 34 | 1,3,5-(CH$_3$)$_3$ | Het10 | H | A1 | B1 | 2,4-Cl$_2$ | 145-150 |
| 35 | 1,5-(CH$_3$)$_2$-3-CF$_3$ | Het10 | H | A1 | B1 | 2,4-Cl$_2$ | 129 |
| 36 | 1-Ac-3,5-(CH$_3$)$_2$ | Het10 | H | A1 | B1 | 2,4-Cl$_2$ | 128-129 |
| 37 | 2,4-(CH$_3$)$_2$ | Het14 | H | A1 | B1 | 2,4-Cl$_2$ | 95-97 |
| 38 | 2-CH$_3$-4-CF$_3$ | Het14 | H | A1 | B1 | 2,4-Cl$_2$ | 136 |
| 39 | 2-CF$_3$ | Het2 | H | A3 | B5 | 3-CF$_3$-4-(3-CF$_3$—Ph)-5-CH$_3$ | nD = 1.4682 (26.0° C.) |
| 40 | 2-Cl | Het2 | H | A3 | B5 | 3-CF$_3$-4-(4-Cl—Ph)-5-CH$_3$ | amorphous |
| 41 | 2-Cl | Het2 | H | A3 | B5 | 3,4,5-Br$_3$ | amorphous |
| 42 | 2-CF$_3$ | Het2 | H | A3 | B5 | 3,4,5-Br$_3$ | 117-119 |
| 43 | 3-CF$_3$ | Het4 | H | A3 | B5 | 3-CF$_3$-4,5-Cl$_2$ | 81-84 |
| 44 | 2-Cl | Het2 | H | A6 | B2 | 3-Cl-5-CF$_3$ | 126 |
| 45 | 2-Cl | Het2 | H | A1 | B1 | 2-Cl-4-O(5-CF$_3$—Py-2-yl) | 127-129.1 |
| 46 | 2-SOCH$_3$ | Het2 | H | A3 | B5 | 3,4,5-Br$_3$ | amorphous |
| 47 | 3-I | Het4 | H | A2 | B1 | 2,4-Cl$_2$ | 160.9-161.8 |
| 48 | 3-CH$_3$ | Het4 | H | A1 | B1 | 4-(4-OCF$_3$—Ph) | 122-123 |
| 49 | 3-CF$_3$ | Het4 | H | A1 | B2 | 3-Cl-4-(4-OCF$_3$—Ph) | 124-125 |
| 50 | 2-CH$_3$ | Het17 | H | A1 | B1 | 2,4-Cl$_2$ | 106-107 |

The endoparasite control agent of the present invention has excellent anti-endoparasite effect, and exerts appropriate control effect against endoparasites. The animal for which the endoparasite control agent of the present invention can be used is a human, an animal of non-human mammalian or avian species, and a fish. Exemplary members of the non-human mammalian species include domestic animals, such as pigs, horses, cattle, sheep, goats, rabbits, camels, water buffalos, deer, mink and chinchillas; pet animals, such as dogs, cats and monkeys; and experimental animals, such as rats, mice, golden hamsters and guinea pigs. Exemplary members of the avian species include domestic fowls, such as chickens, ducks, aigamo ducks (crossbreeds of wild and domestic ducks), quails, domestic ducks, geese and turkeys. Exemplary members of the fish include marine farmed fish such as yellowtail, greater amberjack, red seabream, Japanese sea bass, olive flounder, Japanese pufferfish, striped jack, yellowtail amberjack, spotted knife jaw, cobia and Pacific bluefin tuna; and freshwater farmed fish such as sweetfish, seema, char, carp, crucian carp and rainbow trout.

Human endoparasites against which the endoparasite control agent of the present invention is effective are roughly classified into protozoa and helminths. Examples of the protozoa include, but are not limited thereto, Rhizopoda, such as *Entamoeba histolytica*; Mastigophora, such as *Leishmania, Trypanosoma* and *Trichomonas*; Sporozoea, such as *Plasmodium* and *Toxoplasma*; and Ciliophora, such as *Balantidium coli*. Examples of the helminths include, but are not limited thereto, Nematoda, such as *Ascaris lumbricoides, Anisakis, Toxocara canis, Trichostrongylus* spp., *Enterobius vermicularis*, hookworms (for example, *Ancylostoma duodenale, Necator americanus, Ancylostoma braziliense*, etc.), *Angiostrongylus* spp., *Gnathostoma* spp., filarial worms (filaria, *Wuchereria bancrofti, Brugia malayi*, etc.), *Onchocerca volvulus, Dracunculus medinensis, Trichinella spiralis* and *Strongyloides stercoralis*; Acanthocephala, such as *Macracanthorhynchus hirudinaceus*; Gordiacea, such as *Gordioidea*; Hirudinea, such as *Hirudo nipponia*; Trematoda, such as *Schistosoma japonicum, Schistosoma mansoni, Schistosoma haematobium, Clonorchis sinensis, Heterophyes heterophyes, Fasciola* spp. and *Paragonimus* spp.; and Cestoda, such as *Diphyllobothrium latum, Sparganum mansoni, Sparganum proliferum, Diplogonoporus grandis*, Taeniidae (for example, *Taeniarhynchus saginatus, Taenia solium, Echinococcus*, etc.), *Hymenolepis* spp., *Dipylidium caninum, Mesocestoides lineatus, Bertiella* spp. and *Nybelinia surmenicola*.

Non-human mammalian or avian endoparasites against which the endoparasite control agent of the present invention is effective are roughly classified into protozoa and helminths. Examples of the protozoa include, but are not limited thereto, Apicomplexa, such as Coccidia (for example, *Eimeria, Isospora, Toxoplasma, Neospora, Sarcocystis, Besnoitia, Hammondia, Cryptosporidium, Caryospora*, etc.), Haemosporina (for example, *Leucocytozoon, Plasmodium*, etc.), Piroplasma (for example, *Theileria, Anaplasma, Eperythrozoon, Haemobartonella, Ehrlichia*, etc.), and others (for example, *Hepatozoon, Haemogregarina*, etc.); Microspora, such as *Encephalitozoon* and *Nosema*; Mastigophora, such as Trypanosomatina (for example, *Trypanosoma, Leishmania*, etc.), Trichomonadida (for example, *Chilomastix, Trichomonas, Monocercomonas, Histomonas*, etc.), and Diplomonadida (for example, *Hexamita, Giardia*, etc.); Sarcodina, such as Amoebida (for example, *Entamoeba histolytica (Entamoeba)* etc.); and Ciliophora, such as *Balantidium coli (Balantidium), Buxtonella* and *Entodinium*.

Examples of the helminths include, but are not limited thereto, Nematoda, such as Ascaridida (for example, *Ascaris suum (Ascaris), Toxocara canis* and *Toxocara cati (Toxocara), Toxascaris leonina (Toxascaris), Parascaris equorum (Parascaris), Ascaridia galli (Ascaridia), Heterakis gallinarum (Heterakis), Anisakis*, etc.), Oxyurida (for example, *Oxyuris equi (Oxyuris), Passalurus ambiguus (Passalurus)*, etc.), Strongylida (for example, *Strongylus vulgaris (Strongylus), Haemonchus contortus (Haemonchus), Ostertagia ostertagi (Ostertagia), Trichostrongylus colubriformis (Trichostrongylus), Cooperia punctata (Cooperia), Nematodirus filicollis (Nematodirus), Hyostrongylus rubidus (Hyostrongylus), Oesophagostomum radiatum (Oesophagostomum), Chabertia ovina (Chabertia), Ancylostoma caninum (Ancylostoma), Uncinaria stenocephala (Uncinaria), Necator americanus (Necator), Bunostomum phlebotomum (Bunostomum), Dictyocaulus viviparus (Dictyocaulus), Metastrongylus elongatus (Metastrongylus), Filaroides hirthi (Filaroides), Aelurostrongylus abstrusus (Aelurostrongylus), Angiostrongylus cantonensis (Angiostrongylus), Syngamus trachea (Syngamus), Stephanurus dentatus (Stephanurus)*, etc.), Rhabditida (for example, *Strongyloides stercoralis (Strongyloides), Micronema*, etc.), Spirurida (for example, *Thelazia rhodesi (Thelazia), Oxyspirura mansoni (Oxyspirura), Spirocerca lupi (Spirocerca), Gongylonema pulchrum (Gongylonema), Draschia megastoma (Draschia), Habronema microstoma (Habronema), Ascarops strongylina (Ascarops), Physaloptera praeputialis (Physaloptera), Gnathostoma spinigerum (Gnathostoma)*, etc.), Filariida (for example, *Dirofilaria immitis (Dirofilaria), Setaria equina (Setaria), Dipetalonema, Parafilaria multipapillosa (Parafilaria), Onchocerca cervicalis (Onchocerca)*, etc.), and Enoplida (for example, *Parafilaria bovicola (Parafilaria), Stephanofilaria okinawaensis (Stephanofilaria), Trichuris vulpis (Trichuris), Capillaria Bovis (Capillaria), Trichosomoides crassicauda (Trichosomoides), Trichinella spiralis (Trichinella), Dioctophyma renale (Dioctophyma)*, etc.); Trematoda, such as Fasciolata (for example, *Fasciola hepatica (Fasciola), Fasciolopsis buski (Fasciolopsis)*, etc.), Paramphistomatidae (for example, *Homalogaster paloniae (Homalogaster)*, etc.), Dicrocoelata (for example, *Eurytrema pancreaticum (Eurytrema), Dicrocoelium dendriticum (Dicrocoelium)*, etc.), Diplostomata (for example, *Pharyngostomum cordatum (Pharyngostomum), Alaria*, etc.), Echinostomata (for example, *Echinostoma hortense (Echinostoma), Echinochasmus*, etc.), Troglotrematoidea (for example, lung flukes *(Paragonimus), Nanophyetus salmincola (Nanophyetus)*, etc.), Opisthorchiida (for example, *Clonorchis sinensis (Clonorchis)* etc.), Heterophyida (for example, *Heterophyes heterophyes (Heterophyes), Metagonimus yokogawai (Metagonimus)*, etc.), Plagiorchiida (for example, *Prosthogonimus ovatus (Prosthogonimus)* etc.), and Schistosomatidae (for example, *Schistosoma japonicum (Schistosoma)* etc.); Cestoda, such as Pseudophyllidea (for example, *Diphyllobothrium nihonkaiense (Diphyllobothrium), Spirometra erinacei (Spirometra)*, etc.), and Cyclophyllidea (for example, *Anoplocephala perfoliata (Anoplocephala), Paranoplocephala mamillana (Paranoplocephala), Moniezia benedeni (Moniezia), Dipylidium caninum (Dipylidium), Mesocestoides lineatus (Mesocestoides), Taenia pisiformis* and *Taenia hydatigena (Taenia), Hydatigera taeniaeformis (Hydatigera), Multiceps multiceps (Multiceps), Echinococcus granulosus (Echinococcus), Echinococcus multilocularis (Echinococcus), Taenia solium (Taenia), Taeniarhynchus saginatus (Taeniarhynchus), Hymenolepis diminuta (Hymenolepis), Vampirolepis nana (Vampirolepis)*, Railli-

*etina tetragona* (*Raillietina*), *Amoebotaenia sphenoides* (*Amoebotaenia*), etc.); Acanthocephala, such as *Macracanthorhynchus hirudinaceus* (*Macracanthorhynchus*) and *Moniliformis moniliformis* (*Moniliformis*); Linguatulida, such as *Linguatula serrata* (*Linguatula*); and other various parasites.

In different designations, examples of the helminths include, but are not limited to, Nematoda, such as Enoplida (for example, *Trichuris* spp., *Capillaria* spp., *Trichomosoides* spp., *Trichinella* spp., etc.), Rhabditida (for example, *Micronema* spp., *Strongyloides* spp., etc.), Strongylida (for example, *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp., etc.), Oxyurida (for example, *Oxyuris* spp., *Enterobius* spp., *Passalurus* spp., *Syphacia* spp., Aspiculuris spp., *Heterakis* spp., etc.), *Ascaridia* (for example, *Ascaris* spp., *Toxascaris* spp., *Toxocara* spp., *Parascaris* spp., *Anisakis* spp., *Ascaridia* spp., etc.), Spirurida (for example, *Gnathostoma* spp., *Physaloptera* spp., *Thelazia* spp., *Gongylonema* spp., *Habronema* spp., *Parabronema* spp., *Draschia* spp., *Dracunculus* spp., etc.), and Filariida (for example, *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., etc.);

Acanthocephala (for example, *Filicollis* spp., *Moniliformis* spp., *Macracanthorhynchus* spp., *Prosthenorchis* spp., etc.); Trematoda including subclasses, such as Monogenea (for example, *Gyrodactylus* spp., *Dactylogyrus* spp., *Polystoma* spp., etc.) and Digenea (for example, *Diplostomum* spp., *Posthodiplostomum* spp., *Schistosoma* spp., *Trichobilharzia* spp., *Ornithbilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantoctyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp., etc.);

Cestoda, such as Pseudophyllidea (for example, *Diphyllobothrium* spp., *Spirometra* spp., *Schistocephalus* spp., *Ligula* spp., *Bothridium* spp., *Diplogonoporus* spp., etc.), and Cyclophyllidea (for example, *Mesocestoides* spp., *Anoplocephala* spp., *Paranoplocephala* spp., *Moniezia* spp., *Thysanosomsa*spp., *Thysanieziaspp.*, *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp., etc.); and others including parasites belonging to Acanthocephala and Linguatulida.

Examples of fish parasites include skin parasites, such as *Neobenedenia girellae*, *Benedenia seriolae*, *Benedenia sekii*, *Benedenia hoshinai*, *Benedenia epinepheli*, *Benedenia girellae*, *Anoplodiscus tai* sp. nov., *Anoplodiscus spari*, *Caligus lalandei*, *Caligus longipedis* and *Pseudocaligus fugu*; and gill parasites, such as *Heteraxine heterocerca*, *Zeuxapta japonica*, *Bivagina tai*, *Heterobothrium okamotoi*, *Heterobothrium tetrodonis*, *Neoheterobothrium hirame* and *Caligus spinosus*. Also included are *Dactylogyrus*, *Pseudodactylogyrus*, *Tetraonchus*, *Gyrodactylus*, *Benedenia*, *Neobenedenia* and *Anoplodiscus*; Polyopisthocotylea, such as *Microcotyle*, *Bivagina*, *Heteraxine*, *Heterobothrium*, *Neoheterobothrium* and *Eudiplozoon*; Trematoda, such as *Diplostomum*, *Galactosomum* and *Paradeontacylix*; and Cestoidea, such as *Bothriocephalus* and *Proteocephalus*.

Also included are Nematoda, such as *Anguillicoloides*, *Philometra* and *Philometroides*; Acanthocephala, such as *Acanthocephalus* and *Longicollum*; Bivalvia (a class of the phylum Mollusca), such as *Margaritifera*; Hirudinea (a class of the phylum Annelida), such as *Limnotrachelobdella*; and Crustacea (a subphylum of the phylum Arthropoda), such as *Ergasilus*, *Lernaea*, *Caligus*, *Argulus*, *Bromolochus*, *Chondrocaushus*, *Lepeophtheirus* (for example, *L. salmonis* etc.), *Elythrophora*, *Dichelestinum*, *Lamproglenz*, *Hatschekia*, *Legosphilus*, *Symphodus*, *Ceudrolasus*, *Pseudoscymnus*, *Lernaeocera*, *Pennella*, *Achthales*, *Basanistes*, *Salmincola*, *Brachiella*, *Epibrachiella* and *Pseudotracheliastes*. Further included are Ergasilidae, Bromolochidae, Chondracanthidae, Caligidae, Dichelestiidae, Phylichthyidae, Pseudocycnidae, Lernaeidae, Lernaeopodidae, Sphyriidae, Cercopidae, Copepodae (for example, Cyclops, fish-lice, etc.), Branchiuriae (carp lice), which includes the family Argulidae containing the genus *Argulus*, Cirripediae (for example, cirripedes, barnacles, etc.) and *Ceratothoa gaudichaudii*. Furthermore included are Ciliophora, such as causative agents of white spot disease (*Ichthyophthirius multifiliis* and *Cryptocaryon irritans*), *Trichodina* sp., *Chilodonella* sp., *Brooklynella hostilis* belonging to the class Kinetofragminophorea, and scuticociliates (*Uronema marinum*, *Philasterides dicentrarchi*, *Miamiensis avidus*, *Uronema nigricans* and *Uronema* sp.).

The endoparasite control agent of the present invention is effective against not only parasites that live in the body of an intermediate or final host, but also parasites that live in the body of a reservoir host. The carboxamide derivative represented by the general formula (I) is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae, and adults. The compound of the present invention is capable of not only combating parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites, fleas, lice, assassin bugs, trombiculid mites, etc.; and the like can be prevented from occurring.

The endoparasite control agent of the present invention can be administered as a pharmaceutical for treatment or prevention of parasitosis in humans, animals of non-human mammalian or avian species and fish. The mode of administration may be oral or parenteral administration. In the case of oral administration, the endoparasite control agent of the present invention can be administered, for example, as a capsule, a tablet, a pill, a powder, a granule, a fine granule, a powder, a syrup, an enteric-coated preparation, a suspension or a paste, or after blended in a liquid drink or feed for animals. In the case of parenteral administration, the endoparasite control agent of the present invention can be administered in a dosage form which allows sustained mucosal or percutaneous absorption, for example, as an injection, an infusion, a suppository, an emulsion, a suspension, a drop, an ointment, a cream, a solution, a lotion, a spray, an aerosol, a cataplasm or a tape.

In the case where the endoparasite control agent of the present invention is used as a pharmaceutical for humans, animals of non-human mammalian or avian species and fish, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight, and such a dose may be administered as a single dose or multiple doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that is used for administration after diluted to a suitable concentration.

For the purpose of reinforcing or complementing the effect of the endoparasite control agent of the present invention, a combined use with any existing endoparasite control agent is possible. In such a combined use, two or more active ingredients may be mixed and formulated into a preparation before administration, or two or more different preparations may be administered separately.

EXAMPLES

Next, the present invention will be illustrated in detail by formulation examples and test examples of the endoparasite control agent of the present invention, but the scope of the present invention is not limited by the following formulation examples and test examples.

In the Examples, the "part (s)" refers to apart (s) by weight.

Formulation Example 1

Emulsion

Ten parts of the carboxamide derivative represented by the general formula (I), 6 parts of Sorpol 355S (surfactant, manufactured by Toho Chemical Industry), and 84 parts of Solvesso 150 (manufactured by Exxon) are uniformly mixed with stirring to give an emulsion.

Formulation Example 2

Ointment

One part of the carboxamide derivative represented by the general formula (I), 50 parts of white beeswax, and 49 parts of white petrolatum are well mixed to give an ointment.

Formulation Example 3

Tablet

Two parts of the carboxamide derivative represented by the general formula (I), 10 parts of vegetable oil (olive oil), 3 parts of crystalline cellulose, 20 parts of white carbon, and 65 parts of kaolin are well mixed and compressed into a tablet.

Formulation Example 4

Injection

Ten parts of the carboxamide derivative represented by the general formula (I), 10 parts of propylene glycol for use as a food additive, and 80 parts of vegetable oil (corn oil) are mixed to give an injection.

Formulation Example 5

Solution

Five parts of the carboxamide derivative represented by the general formula (I), 20 parts of surfactant, and 75 parts of ion exchanged water are well mixed to give a solution.

Test Example 1

In Vitro Measurement of Inhibitory Activity on *Ascaris suum* Succinate-Ubiquinone Reductase (Mitochondrial Complex II)

To a solution containing 50 mM potassium phosphate (pH 7.4) and 0.1% (w/v) sucrose monolaurate, an electron acceptor ubiquinone-2 ($UQ_2$) was added at a final concentration of 60 µM, and the mixture was allowed to stand at 25° C. for 20 minutes. To this, potassium cyanide (final concentration: 2 mM) and mitochondria prepared from adult *Ascaris suum* muscle were added, and thorough mixing was done. To aliquots of the mixture, an inhibitor to be tested was added at various concentrations, and the mixtures were allowed to stand at 25° C. for 3 minutes. The enzymatic reaction was initiated by addition of potassium succinate (final concentration: 10 mM). The enzymatic activity was calculated based on the measurement of change in the absorbance at 278 nm of $UQ_2$ ($\epsilon=1.5\times10^4$ $M^{-1}cm^{-1}$), and $IC_{50}$ was determined from the plot of the inhibition percentage against the inhibitor concentration. The results are shown in Table 2.

TABLE 2

| Compound No. | *Ascaris suum* $IC_{50}$ value (A) |
|---|---|
| 1 | 47 nM |
| 2 | 57 nM |
| 3 | 9.4 nM |
| 4 | 1.3 nM |
| 5 | 26 nM |

TABLE 2-continued

| Compound No. | *Ascaris suum* IC$_{50}$ value (A) |
|---|---|
| 6 | 4.4 nM |
| 7 | 1.1 nM |
| 11 | 3.4 nM |
| 13 | 2.7 nM |
| 14 | 3.3 nM |
| 16 | 1.5 nM |
| 17 | 2.0 nM |
| 18 | 3.1 nM |
| 19 | 1.3 nM |
| 20 | 4.9 nM |
| 21 | 1.3 nM |
| 22 | 1.7 nM |
| 23 | 10 nM |
| 24 | 2.0 nM |
| 25 | 18 nM |
| 26 | 2.9 nM |
| 27 | 2.2 nM |
| 28 | 1.3 nM |
| 29 | 6.7 nM |
| 30 | 6.0 nM |
| 31 | 42 nM |
| 33 | 7.3 nM |
| 41 | 42 nM |
| 42 | 13 nM |
| 43 | 9.9 nM |
| 44 | 20 nM |
| 45 | 4.5 nM |
| 47 | 2.3 nM |
| 50 | 1.6 nM |

As is clear from the results in Table 2, the carboxamide derivatives represented by the general formula (I) and salts thereof showed a strong inhibitory activity on the parasitic succinate-ubiquinone reductase (mitochondrial complex II) (IC$_{50}$ values: 1.1 to 57 nM). Therefore, the carboxamide derivatives and salts thereof are highly active in parasite control.

Test Example 2

In Vivo Activity Test on *Haemonchus* Nematode

In a 96-well plate, twenty L1-stage larvae (*Haemonchus contortus*) per well were maintained so that they could freely move, and solutions of compounds of the present invention dissolved at predetermined concentrations in DMSO (the final concentration of DMSO was 0.78% (v/v)) were added at 0.5 μl/well each. The plate was kept under the conditions of 27° C./95% RH for 4 days. The motor ability of the larvae was examined and the concentration required for 50% inhibition of the motor ability (EC$_{50}$) was determined. Based on the EC$_{50}$ value, the activity against the *Haemonchus* nematode was graded according to the criterion shown below. The results are shown in Table 3.
Grading Criterion
A: The EC$_{50}$ value is lower than 0.5 ppm.
B: The EC$_{50}$ value is 0.5 ppm or higher but lower than 5 ppm.
C: The EC$_{50}$ value is 5 ppm or higher.

TABLE 3

| Compound No. | Grade |
|---|---|
| 1 | A |
| 3 | A |
| 6 | A |
| 7 | A |

TABLE 3-continued

| Compound No. | Grade |
|---|---|
| 9 | A |
| 13 | A |
| 15 | A |
| 16 | A |
| 17 | A |
| 19 | A |
| 21 | A |
| 22 | A |
| 23 | A |
| 24 | A |
| 25 | A |
| 28 | A |
| 33 | A |
| 35 | B |
| 38 | B |
| 48 | A |
| 49 | A |

As is clear from the results in Table 3, the carboxamide derivatives represented by the general formula (I) and salts thereof were graded as B or higher in the in vivo test using the *Haemonchus* nematode. Therefore, the carboxamide derivatives and salts thereof also have a strong and high in vivo activity in parasite control.

The invention claimed is:
1. A method for controlling endoparasites, comprising orally or parenterally administering an effective amount of an endoparasite control composition comprising a compound of the general formula (I):

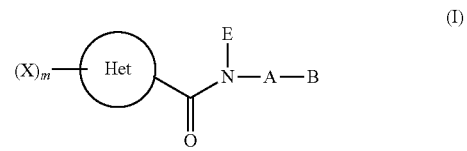

wherein

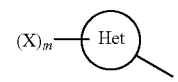

is any moiety selected from the group consisting of Het4 to Het7:

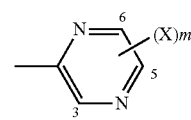

Het 4

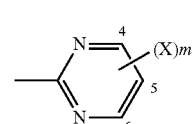

Het 5

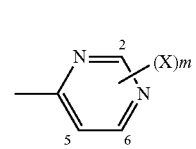

Het 6

Het 7

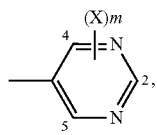

wherein each X is trifluoromethyl,
m is an integer of 1
the numbers on each ring represent positions where the ring can be substituted by X and the free bond extending from each ring is a bond between Het and the carbonyl group in the general formula (I), A represents a ($C_1$-$C_8$) alkylene group; or a substituted ($C_1$-$C_8$) alkylene group having one or more substituents selected from a halogen atom, a ($C_1$-$C_6$) alkyl group and a ($C_3$-$C_6$) cycloalkyl group, with the proviso that the ($C_1$-$C_8$) alkylene group and the substituted ($C_1$-$C_8$) alkylene group can be modified by incorporation, into the carbon chain, of at least one group selected from —O—, —S—, —SO—, —SO$_2$— and —N(R)—, wherein R represents a hydrogen atom, a ($C_1$-$C_6$) alkyl group, a ($C_3$-$C_6$) cycloalkyl group, a ($C_1$-$C_6$) alkylcarbonyl group or a ($C_1$-$C_6$) alkoxycarbonyl group, and with the proviso that when the alkylene group or the substituted alkylene group having one or more substituents is a ($C_3$-$C_6$) or ($C_3$-$C_8$) alkylene group, or a ($C_2$-$C_6$) or ($C_2$-$C_8$) alkylene group modified by incorporation, into the carbon chain, of at least one group selected from —O—, —S—, —SO—, —SO$_2$— and —N(R)—, A can form a cyclic structure, wherein the cyclic structure is cyclopropane, cyclobutane, cyclopentane or cyclohexane, E represents a hydrogen atom; a ($C_1$-$C_6$) alkyl group; a ($C_3$-$C_6$) cycloalkyl group; a ($C_1$-$C_6$) alkoxy ($C_1$-$C_6$) alkyl group; a ($C_1$-$C_6$) alkylcarbonyl group; or a ($C_1$-$C_6$) alkoxycarbonyl group, and B represents any of the moieties represented by the following B1 to B8:

B1

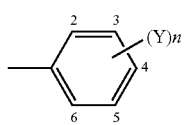

B2

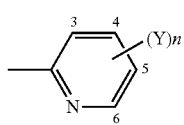

B3

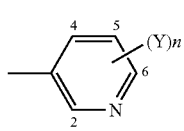

B4

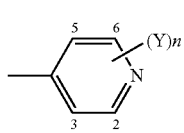

B5

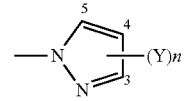

B6

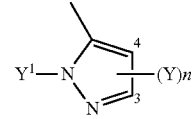

B7

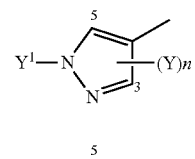

B8

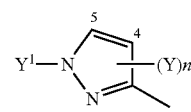

wherein each Y can be the same or different, and represents a halogen atom; a cyano group; a nitro group; a hydroxy group; a ($C_1$-$C_6$) alkyl group; a halo ($C_1$-$C_6$) alkyl group; a ($C_2$-$C_6$) alkenyl group; a halo ($C_2$-$C_6$) alkenyl group; a ($C_2$-$C_6$) alkynyl group; a halo ($C_2$-$C_6$) alkynyl group; a ($C_1$-$C_6$) alkoxy group; a halo ($C_1$-$C_6$) alkoxy group; a ($C_1$-$C_6$) alkoxy ($C_1$-$C_6$) alkoxy group; a ($C_2$-$C_6$) alkenyloxy group; a halo ($C_2$-$C_6$) alkenyloxy group; a ($C_2$-$C_6$) alkynyloxy group; a halo ($C_2$-$C_6$) alkynyloxy group; a ($C_1$-$C_6$) alkylthio group; a halo ($C_1$-$C_6$) alkylthio group; a ($C_1$-$C_6$) alkylsulfinyl group; a halo ($C_1$-$C_6$) alkylsulfinyl group; a ($C_1$-$C_6$) alkylsulfonyl group; a halo ($C_1$-$C_6$) alkylsulfonyl group; a ($C_1$-$C_6$) alkoxycarbonyl group; a ($C_1$-$C_6$) alkoxyimino ($C_1$-$C_3$) alkyl group; a ($C_3$-$C_{30}$) trialkylsilyl group; a mono ($C_1$-$C_6$) alkylsulfonylamino group; a mono halo ($C_1$-$C_6$) alkylsulfonylamino group; a phenyl group; a substituted phenyl group having one or more substituents selected from group Z substituents on the ring; a phenoxy group; a substituted phenoxy group having one or more substituents selected from group Z substituents on the ring; a heterocyclic group; a substituted heterocyclic group having one or more substituents selected from group Z substituents on the ring; a heterocycloxy group; or a substituted heterocycloxy group having one or more substituents selected from group Z substituents on the ring, the group Z substituents are a halogen atom; a cyano group; a nitro group; a ($C_1$-$C_6$) alkyl group; a halo ($C_1$-$C_6$) alkyl group; a ($C_2$-$C_6$) alkenyl group; a halo ($C_2$-$C_6$) alkenyl group; a ($C_2$-$C_6$) alkynyl group; a halo ($C_2$-$C_6$) alkynyl group; a ($C_1$-$C_6$) alkoxy group; a halo ($C_1$-$C_6$) alkoxy group; a ($C_2$-$C_6$) alkenyloxy group; a halo ($C_2$-$C_6$) alkenyloxy group; a ($C_2$-$C_6$) alkynyloxy group; a halo ($C_2$-$C_6$) alkynyloxy group; a ($C_1$-$C_6$) alkylthio group; a halo ($C_1$-$C_6$) alkylthio group; a ($C_1$-$C_6$) alkylsulfinyl group; a halo ($C_1$-$C_6$) alkylsulfinyl group; a ($C_1$-$C_6$) alkylsulfonyl group; a halo ($C_1$-$C_6$) alkylsulfonyl group; a ($C_1$-$C_6$) alkoxycarbonyl group; and a ($C_1$-$C_6$) alkoxyimino ($C_1$-$C_3$) alkyl group, $Y^1$ represents a ($C_1$-$C_6$) alkyl group, n represents an integer of 0 to 5, with the proviso that when n is an integer of 2 to 5, two adjacent Y groups can join together to form a ($C_3$-$C_5$) alkylene group; a ($C_3$-$C_5$) alkenylene group; a ($C_2$-$C_4$) alkyleneoxy group; a ($C_1$-$C_3$) alkylene dioxy group; or a halo ($C_1$-$C_3$) alkylene dioxy group, and the numbers on each ring represent positions where the ring can be substituted by Y and the free bond extending from each ring is a bond between A and B, or a salt thereof as an active ingredient to a non-human mammal or a bird, wherein the endoparasite is protozoa or helminths.

2. The method according to claim 1, wherein the effective amount of the endoparasite control agent is orally or parenterally administered to a non-human mammal.

3. The method according to claim 2, wherein the non-human mammal is a domestic animal.

4. The method according to claim 1, wherein

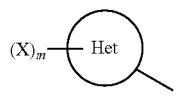

is Het 4.

5. The method according to claim 1, wherein A is a ($C_1$-$C_8$) alkylene group; or a substituted ($C_1$-$C_8$) alkylene group having one or more substituents selected from a halogen atom, a ($C_1$-$C_6$) alkyl group and a ($C_3$-$C_6$) cycloalkyl group.

6. The method according to claim 1, wherein B is B1, B2 or B5.

7. The method according to claim 1, wherein

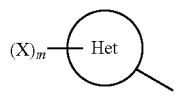

is Het4,
A is a ($C_1$-$C_8$) alkylene group; or a ($C_1$-$C_8$) alkylene group substituted by a ($C_1$-$C_6$) alkyl group,
E is a hydrogen atom,
B is B1, B2 or B5,
each Y can be the same or different, and is a halogen atom; a ($C_1$-$C_6$) alkyl group; a halo ($C_1$-$C_6$) alkyl group; a phenyl group; a substituted phenyl group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a phenoxy group; a substituted phenoxy group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a pyridyl group; a substituted pyridyl group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a pyridyloxy group; or a substituted pyridyloxy group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring, and
n is an integer of 1 to 3.

8. The method according to claim 1, wherein

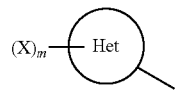

is Het4,
A is a ($C_1$-$C_8$) alkylene group; or a ($C_1$-$C_8$) alkylene group substituted by a ($C_1$-$C_6$) alkyl group,
E is a hydrogen atom,
B is B1,
each Y can be the same or different, and is a halogen atom; a ($C_1$-$C_6$) alkyl group; a halo ($C_1$-$C_6$) alkyl group; a phenyl group; a substituted phenyl group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a phenoxy group; a substituted phenoxy group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a pyridyl group; a substituted pyridyl group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring; a pyridyloxy group; or a substituted pyridyloxy group having one or more substituents selected from a halogen atom, a ($C_1$-$C_6$) alkyl group, a halo ($C_1$-$C_6$) alkyl group, a ($C_1$-$C_6$) alkoxy group and a halo ($C_1$-$C_6$) alkoxy group on the ring, and
n is an integer of 1 to 3.

* * * * *